United States Patent [19]
Seshadri et al.

[11] Patent Number: 5,981,685
[45] Date of Patent: Nov. 9, 1999

[54] ORGANOTIN SULFONATE CATALYSTS AND THEIR MANUFACTURE

[75] Inventors: Sri R. Seshadri, Newtown; William D. Honnick, Exton; Melvin H. Gitlitz, Berwyn, all of Pa.

[73] Assignee: ELF Atochem North America, Inc., Philadelphia, Pa.

[21] Appl. No.: 09/093,930

[22] Filed: Jun. 9, 1998

Related U.S. Application Data

[60] Provisional application No. 60/052,031, Jul. 9, 1997.

[51] Int. Cl.$^6$ .................................................. C08G 18/08
[52] U.S. Cl. ............................................................... 528/58
[58] Field of Search .......................................... 528/44, 58

[56] References Cited

U.S. PATENT DOCUMENTS

| | | | |
|---|---|---|---|
| 5,606,103 | 2/1997 | Trapasso et al. | 560/217 |
| 5,770,672 | 6/1998 | Gitlitz et al. | 528/58 |

*Primary Examiner*—Terressa Mosley
*Attorney, Agent, or Firm*—Stanley A. Marcus; Nicholas J. Debenedictis

[57] ABSTRACT

Dual cure organotin salts of strong organic acids, the use of such salts as catalysts and an improved process for producing the catalysts are provided. The catalysts are capable of effectively catalyzing esterification and transesterification reactions and urethane, silicone, melamine, ester and acrylic forming reactions and can simultaneously catalyze more than one reaction in a mixture of urethane, silicone, amino, ester and acrylic polymer forming reactants to produce a polymer mixture.

17 Claims, No Drawings

ORGANOTIN SULFONATE CATALYSTS AND THEIR MANUFACTURE

This application claims benefit of provisional application Ser. No. 60/052,031 filed Jul. 9, 1997.

BACKGROUND OF THE INVENTION

1. Field of the Invention

The invention is directed to organotin sulfonate catalysts, polymers produced with organotin catalysts, and manufacture of organotin catalysts.

2. Description of Related Art

Catalysts are commonly used in the polymerization and cross linking reactions of monomeric or resinous materials to form polymers. The catalysts, polymerizable components, and other additives may be in the form of coatings, particles, articles, solutions, or dispersions. The compositions may be manipulated and polymerized as "neat" compositions, i.e. in the absence of solvents or carriers, as organic solutions or as water dispersed or emulsified compositions. Each composition has it's own strengths and weaknesses.

The chemistry of the polymerizable components is the primary factor in selecting a specific catalyst to use. However, it is difficult to predict the suitability of a catalyst without experimental verification. Often a catalyst that is effective for catalyzing one type of reaction, i.e. polyurethane polymer formation, is not be well suited for catalyzing a different type of reaction, i.e. butylated melamine polymerization. Accordingly, when polyurethane forming reactants and polyamine (e.g. melamine) forming reactants are combined into a single formulation, two different catalysts are added, one for the polyurethane forming reaction and another for the melamine forming reaction so that the two different reactions can proceed simultaneously at reasonably comparable reaction rates.

Some, polystannoxanes are known and have been shown to have catalytic activity for certain reactions; see for example:

"Distannoxane as reverse micelle type catalyst; novel solvent effect on reaction rate of transesterification" Junzo Otera, Shingi Ioka; and Hitosi Nozaki, Journal of Organic Chemistry, 1989, 54, 4013–4014.

"Novel template effect of distannoxane catalysts in highly efficient transesterification and esterification", Juno Otera, Nobuhisa Dan-oh and Hitosi Noaki, Journal of Organic Chemistry, 1991, 56, 5307–5311.

While polystannoxanes have been disclosed, their sulfonate derivatives do not appear in the prior art. For example, U.S. Pat. No. 2,720,507 discloses a wide variety of classes of organotin compounds which are said to be useful as catalysts in the preparation of polyesters. However polystannoxanes sulfonates are not disclosed.

U.S. Pat. No. 3,681,271, discloses the use of tristannoxanes as catalysts in the preparation of urethane foams. No organotin sulfonates are disclosed.

U.S. Pat. No. 3,676,402. This patent discloses the use of octaalkylstannoxanes as catalysts in urethane systems comprising blocked isocyanates. No organotin sulfonates are disclosed.

U.S. Pat. No. 3,194,770, discloses the use of a wide variety of classes of organotin compounds useful as catalysts in curing compositions, particularly foams. Stannoxanes are disclosed but polystannoxanes sulfonates are not disclosed.

Mononuclear (monomeric) organotin sulfonates have been disclosed as a composition of matter and their use as polyurethane foam catalysts has also been disclosed. For example:

U.S. Pat. No. 3,095,434 discloses a wide range of di and tri organotin sulfonates and describes their use as pesticides. Catalyst utility for polyurethane foams is also disclosed.

U.S. Pat. No. 4,286,073 claims di and trialkytin sulfonates as urethane foam catalysts.

U.S. Pat. No. 4,611,049 discloses a process for producing aromatic polyesters. The catalyst may be an organotin compound used with a sulfonic acid promoter but the catalyst and promoter do not constitute an organotin sulfonate. The ability for mononuclear organotin sulfonates to effectively catalyze several different polymerization reactions simultaneously has not been disclosed.

SUMMARY OF THE INVENTION

The invention provides an organotin sulfonate catalyst capable of effectively catalyzing polymerization, esterification, transesterification, and condensation reactions individually or more than one such reaction simultaneously. Novel organotin sulfonate catalysts are provided that comprise polystannoxane salts containing an organosulfonate group and corresponding to the following formula:

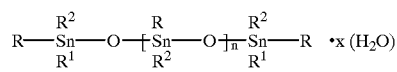

wherein
- each R is independently selected from the group consisting of alkyl having from 1 to 20 carbon atoms, aryl and alkaryl;
- each $R^1$ is independently selected from the group consisting of OR, OH, OOCR, halogen, and a derivative of a strong organic acid having a pKa of less than 1 provided that at least one selection for $R^1$ is $OSO_2R$ with each R having the same meaning as above;
- each $R^2$ being independently selected from the same groups as R and $R^1$;
- n is an integer having an average value from 0 to 20; and,
- x indicates the quantity of water of hydration which may be as low as 0 and approach infinity when the compound is in an aqueous solution.

The above formula is referred to at times herein as "Formula 1".

Good catalytic activity and dual cure capabilities have also been discovered for an expanded Formula 1 and for monomeric organotins of the formula:

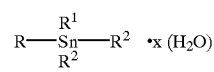

wherein R, $R^2$, and x have the same values as above for Formula 1 and $R^1$ is independently selected from the group consisting of OR, OH, OOCR, halogen, and a derivative of a strong organic acid having a pKa of less than 1, with R having the same meaning as above, provided that at least one $R^1$ is derived from an organic acid having a pKa less than 1. (hereinafter referred to as Formula 2).

The expanded version of Formula 1 for which catalytic and dual cure uses has been discovered is:

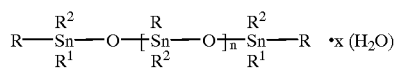

wherein
- each R is independently selected from the group consisting of alkyl having from 1 to 20 carbon atoms, aryl and alkaryl;
- each $R^1$ is independently selected from the group consisting of OR, OH, OOCR, halogen, and a derivative of a strong organic acid having a pKa of less than 1, with R having the same meaning as above; provided that at least one $R^1$ is derived from an organic acid having a pKa less than 1;
- each $R^2$ being independently selected from the same groups as R and $R^1$;
- n is an integer having an average value from 0 to 20; and,
- x indicates the quantity of water of hydration which may be as low as 0 and approach infinity when the compound is in an aqueous solution.

The above formula is referred to at times herein as "Expanded Formula 1". The difference between Formula 1 and Expanded Formula 1 is in the definition of $R^1$. In Expanded Formula 1, at least one value for $R^1$ must be derived from an organo acid having a pKa value less than 1 while in Formula 1 the derivative of the strong organo acid is limited to $OSO_2R$. Therefore, Expanded Formula 1 includes all of the compounds of Formula 1 plus those compounds having $R^1$ values other than $OSO_2R$.

It has also been discovered that the organotin compounds of Formula 1, Expanded Formula 1 and Formula 2 are capable of simultaneously catalyzing more than one polymerization reaction for producing urethane, urea, silicone, or amino polymers. Simultaneously catalyzing more than one such reaction is referred to herein as "dual cure".

A novel process is also provided for the production of the compounds of Formula 1, Expanded Formula 1 and Formula 2 using water and at least one additional polar solvent. The process produces organotins having novel physical properties.

DETAILED DESCRIPTION

The novel organotin sulfonates are polystannoxanes salts of a strong organic acid depicted in Formula 1. The organo tin compounds depicted by Formula 1, Expanded Formula 1 and Formula 2 have been discovered to be excellent catalysts for esterification or transesterification reactions or polymerization reactions for producing urethane, urea, silicone, and amino polymers. While organotin catalysts of the present invention can be depicted by the above formulas, when produced, a mixture of organo tin compounds is obtained that can be analyzed and theorized to conform to the above structural formulas with the values for n and x being average values. While analysis of compounds of the present invention are consistent with the structures depicted by Formula 1, Expanded Formula 1 or Formula 2, the analysis are also consistent with describing the compounds by comparable empirical formulas given hereinafter. The structural formulas and the empirical formulas are considered equivalent for the purposes of the present invention. Values for x in Formula 1, Expanded Formula 1 or Formula 2 can vary significantly, for example x, can have an average value from 0 to 250 and for water soluble species of Formula 1, Expanded Formula 1 and Formula 2, the upper limit of x can be much larger than 250 and approach infinity in an aqueous solution. In a water solution, equivalent formulas are the formulas without the "$x(H_2O)$".

Preferably at least one selection for $R^1$ in Formula 1, Expanded Formula 1 and Formula 2 is from the group consisting of:

(a), $OSO_2R$, wherein R is independently selected from the group consisting of alkyl having from 1 to 20 carbon atoms, aryl and alkaryl;

(b), R COO wherein R is an alkyl or aryl group in which the carbon atom bonded to the COO group contains at least one F, Cl, Br, I, CN attached to it;

(c), $RPO_3H$ wherein R is independently selected from the group consisting of alkyl having from 1 to 20 carbon atoms, aryl and alkaryl;

(d) $RCrO_4H$ wherein R is independently selected from the group consisting of alkyl having from 1 to 20 carbon atoms, aryl and alkaryl; and, (e) F; $NO_3$; $ClO_4$; and, $(NO)_2C_6H_2OH$.

When one selection for $R^1$ in Expanded Formula 1 or Formula 2 is from this preferred group, the requirement in the formula that at least one value for $R^1$ be derived from a strong organic acid having a pKa less than 1 has been satisfied except when the selection is F, $NO_3$, or $ClO_4$. Most preferred selections for $R^1$ is p-toluene sulfonate and methyl sulfonate. The preferred selections for R and $R^2$ is butyl. The preferred values for n is from 0 to 3 in Formula 1 and Expanded Formula 1.

SYNTHESES

Synthesis of monostannoxane sulfonates of Formula 2 is disclosed in U.S. Pat. No. 3,095,434 which disclosure is incorporated herein by reference.

The polystannoxane sulfonates of Formula 1 and Expanded Formula 1 have been synthesized in several different ways, such as:

1. 130.0 grams (0.52 moles) of dibutyltin oxide (DBTO), 99.34 grams (0.52 moles) of p-toluene sulfonic acid hydrate, and heptane were added to a 1 liter flask fitted with a thermometer, paddle stirrer, Dean and Stark separator, and a condenser. The mixture was heated to reflux while being agitated. The water produced by the reaction and the water of hydration from the p-toluene sulfonic acid was removed via distillation. The condensed vapors were collected in the Dean and Stark separator, in which the lower aqueous phase was removed and the upper organic phase was returned to the reaction flask.

After 3 hours at reflux, the heat was removed and the mixture allowed to cool to room temperature. The solids were filtered and dried in vacuo at 60° C. for 12 hours. The solid product had a "tacky" consistency. The product analyses was:

| Analyses: | Found | |
|---|---|---|
| % Sn | 28.8 | |
| Acid Number | 134 | (mg KOH/g) |
| % H$_2$O | 2.74 | (Karl-Fisher) |
| % LOD | 0.59 | (100° C., 75 torr, 2 hrs) |

This produced a polystannoxane that can be depicted by Formula I in which R and R$^2$ are butyl, R$^1$ is p-toluene sulfonate, n is between 0 and 0.1 and x is between 0 and 0.3. Likewise, the analysis of the reaction product is consistent with a polystannoxane of the empirical formula R$_2$SnAO—[R$_2$SnO]$_x$—SnR$_2$A (H$_2$O)$_n$ in which all the selections for R are butyl, A is p-toluene sulfonate, the derivative of a strong organic acid, x is between 0 and 0.1 and n is about 0.3. Whether a product such as the one produced by this synthesis and identified by the above analysis, is depicted by the empirical formula or by Formula 1, they are considered equivalent for the purposes of this invention.

2. 124.45 grams (0.50 moles) of dibutyltin oxide, 95.11 grams (0.50 moles) of p-toluene sulfonic acid hydrate, 150.0 grams of 2-propanol, and 150 grams of deionized water were added to a 1 liter flask fitted with a thermometer, paddle stirrer, and condenser. The mixture was heated to reflux while being agitated and held at reflux for 1 hour. Heating was stopped, and the reaction mixture was allowed to cool to about 25° C. The solid product was filtered and dried at 50° C. under 50 torr of vacuum for 2.5 hours. In contrast to the product of syntheses 1, the product produced in the mixed solvent system of water and an organic polar solvent produced a product that was easily filtered and was readily dried to a granular crystalline solid that was not "tacky".

| Analyses: | Found | |
|---|---|---|
| % Sn | 27.3 | |
| Acid Number | 128 | (mg KOH/g) |
| % H$_2$O | 8.46 | (Karl-Fisher) |
| % LOD | 5.64 | (100° C., 75 torr, 2 hrs) |

The analysis confirms that the reaction product is a polystannoxane of Formula 1 wherein each R is butyl and each R$^1$ is p-toluene sulfonate, n has an average value of between 0 and 0.1, and x has a value of 3.1. Likewise, the analyses is consistent with a polystannoxane reaction product of the empirical formula R$_2$SnAO—[R$_2$SnO]$_x$—SnR$_2$A (H$_2$O)$_n$ in which all the selections for R are butyl, A is the derivative for a strong organic acid and is p-toluene sulfonate, x is between 0 and 0.2 and n is about 3.

3. 124.44 grams (0.50 moles) of dibutyltin oxide, 95.11 grams (0.50 moles) of p-toluene sulfonic acid hydrate, 150.0 grams of 2-propanol, and 150 grams of deionized water were added to a 1 liter flask fitted with a thermometer, paddle stirrer, and condenser. The mixture was heated to reflux while being agitated and held at reflux for 1 hour. Heating was stopped, and the reaction mixture was allowed to cool to about 25° C. The solid product was filtered and dried at 80° C. under 50 torr of vacuum for 8 hours. The solid was easy filter out and was readily dried to a granular crystalline solid that was not "tacky".

| Analyses: | Found | |
|---|---|---|
| % Sn | 28.3 | |
| Acid Number | 131 | (mg KOH/g) |
| % H$_2$O | 4.28 | (Karl-Fisher) |
| % LOD | 1.87 | (100° C., 75 torr, 2 hrs) |

This produces a polystannoxane of the Formula 1 wherein each R is butyl and each R$^1$ is p-toluene sulfonate, n has an average value of between 0 and 0.1, and x has a value of about 1.0. Likewise, the analyses of the reaction product is consistent with a polystannoxane of the empirical formula R$_2$SnAO—[R$_2$SnO]$_x$—SnR$_2$A (H$_2$O)$_n$ in which all the selections for R are butyl, A is the derivative for a strong organic acid and is p-toluene sulfonate, x is between 0 and 0.2 and n is about 1.

The preferred synthesis is with at least two polar solvents as exemplified in synthesis 2 and 3. Preferably one solvent is water and another polar solvent is an alcohol particularly C$_1$ to C$_5$ aliphatic alcohols especially methanol, ethanol, propanol, and butanol (including isomers). Synthesis in a solvent mixture of water an at least one additional organic polar solvent produces a crystalline form of the organotin compounds of Formula 1, Expanded Formula 1 and Formula 2 having unique properties permitting the compounds to be ready dried into a non tacky crystalline powder. Preferably, water constitutes at least about 25% of the polar solvent mixture with 50% being particularly preferred.

ESTERIFICATION AND TRANSESTERIFICATION

When at least one of the values for R$^1$ in Formula 1, Expanded Formula 1 or Formula 2 is OSO$_2$R the resulting organotin sulfonate either the polystannoxane, monomeric stannoxane or organotin sulfonate is surprisingly effective as a catalyst for esterification and transesterification reactions in addition to urethane, silicone and amino polymerization or condensation reactions.

DUAL CURE

Good catalytic activity and dual cure capabilities have also been discovered for organotin catalysts of Formula 1, Expanded Formula 1 and Formula 2. The catalysts of Expanded Formula 1 and Formula 2 possess the surprising ability to simultaneously catalyze two or more urethane, ester, silicone, and amino forming reactions when the reactants for more then one urethane, silicone, amino and ester forming reactions are present in a single composition. Such simultaneous catalysis is referred to herein as "dual cure" catalysis. In order for a catalyst to simultaneously catalyze two different reactions in a mixture of reactants for each reaction, the catalyst must catalyze each reaction at reasonably equivalent reaction rates so that neither reaction reaches substantial completion significantly before the other reaction. In other words if one reaction reaches a desired degree of cure or completion in a certain amount of time with a specific catalyst, then the other desired reaction should reach a comparable degree of cure in an amount of time that is an order of magnitude and preferable within + or −50% of the first reaction time with the same concentration of the same catalyst. This can be determined by testing each desired reaction separately with the target catalyst. In contrast, current commercial standard is to use at least two different catalysts for catalyzing each reaction while a single organotin catalysts of the present invention can perform like the different commercial standard catalysts for each reaction. Therefore a single catalyst of Formula 1, Expanded Formula 1 or Formula 2 can effectively catalyze more than one such reaction simultaneously. A particular advantage of dual cure capabilities of a catalyst is in coatings of two or more layers. Typically, coatings such as automotive paints are applied in several layers such as a pigmented under layer and a clear top coat layer. The coating formulation used for the under layer is a pigmented composition containing urethane, silicone and/or melamine forming reactants and the top clear coat often contains polyurethane and/or melamine forming reactants without pigments. With a dual cure catalyst of the present invention, the catalyst can be added to the coating formulation for the first or under layer with the second layer or upper coat being applied on top of the under layer and before curing of the under layer, with the upper coating not containing or containing relatively little catalyst. Upon curing, the under layer tends to cure faster because of the presence of a greater effective amount of catalyst. During curing of the under layer, migration of catalyst into the top or upper layer occurs promoting curing of the top layer. This also promotes strong inter-layer bonding and allows for release of volatiles released during curing of the under layer to be released through the still uncured upper layer. While it is preferred for the upper layer not to contain catalyst, it is sufficient for the upper layer to contain relatively less catalyst then the under layer. Relatively less catalyst is an amount of catalyst that results in longer curing time for the upper layer such as more than twice the curing time of the under layer. A multilayer coating system using the catalysts of the present invention and a gradation in catalyst concentration between the layers has the advantage of a single cure step after several layers have been applied along with migration of the catalysts upwardly among the layers during curing to increase the effective catalyst concentration of upper layers.

USE OF CATALYST

The catalyst is employed in a catalytically effective amount usually from about 0.01% to about 5% and especially from about 0.05% to about 2% based on the weight of metal in the catalyst and based on total weight of polymerizable solids. All percentages or other proportions given herein are based on weight unless otherwise stated. The catalysts of Formula 1, Expanded Formula 1 and Formula 2 can be used in combination with other catalysts especially tin and zinc containing catalyst such as dibutyl tin dilaurate, dibutyltin oxide and zinc neodecanoate.

REACTANTS

Transesterification and Esterification Reactants

Reactants that undergo esterification and transesterification are well known to those skilled in those arts. For example reactants for transesterification include Monomeric esters and polymeric esters of carboxylic acid reacted with monomeric or polymeric alcohols. Reactants for esterification include Mono and polycarboxylic acids reacted with monomeric or polymeric alcohols.

Polymer Forming Reactants

Reactants for forming polymers such as urethane, urea, silicone, and amino polymers are well known to those skilled in the polymer art. Reactants for urethane polymers are usually aromatic and diphatic isocyanates and blocked isocyanates reacted with polyhydroxy and amino compounds. For silicone polymers, reactants are usually alkoxy silane (and alkoxy acrylosilane) reacted with a polymeric hydroxy compound. For amino resins such as melamine polymers, typical reactants to produce amino resins consist of condensation product reactants like urea, melamine, carbamyl methylated melamines, glycoluril or benzoguanamine usually reacted with formaldehyde or buranol. Also acrylic carbamates reacted with melamine forming reactants.

Additional (Optional) Ingredients

Additional ingredients may be added to the compositions disclosed herein of the type usually added to coating or polymer compositions such as cocatalysts, pigments, fillers, extenders and polymer modifiers.

EXAMPLES

Example A

A typical formulation for a simple urethane reaction was prepared utilizing a polyol (neophenyl alcohol) and an isocyanate (Cyclohexylisocyanate) to form a urethane. Neither the isocyanate nor the alcohol are multifunctional and accordingly a urethane rather then a polyurethane was formed. Such a straight forward reaction is used to screen catalysts for urethane catalytic activity. The catalytic activity of several catalysts of the present invention (Formula 1 and Formula 2) as identified in Table A were compared to dibutyltin dilaurate, a commercial standard catalyst for such a urethane reaction. Comparisons were done on an equal weight of tin basis for calculating the amount of catalyst added to the formulation. After catalyst addition into the formulation, the reaction was allowed to proceed at room temperature. The extent of isocyanate consumption (urethane formation) was monitored by FTIR as a function of time. From first order kinetics, the relative rate of reaction as determined. The higher the rate, the faster the urethane formation. None of the catalysts of the present invention were effective as urethane catalysts for the reaction of an alcohol with a isocyanate in comparison to a well known urethane catalyst, dibutyltin dilaurate. This confirms the general belief in the art that acid groups tend to retard the urethane reaction and would lead one to conclude that the catalysts of the present invention were not effective catalysts for urethane forming reactions. The following examples are illustrative of the invention and the preferred embodiments.

Example 1

Catalytic activity for a typical automotive polyurethane refinishing was evaluated. In view of the results of Example A, catalysts of the present invention (Formula 1, Expanded Formula I and Formula 2) would not be expected to be effective when compared with a present industrial standard catalyst, dibutyltin dilaurate (DBTDL). Aliquots of a formulation of an acrylic based polyester polyol and hexane diisocyanate were prepared with xylene and ketones as solvents each containing sufficient catalyst to constitute 0.14% catalyst based on the weight of tin and based on the total weight of solids in the formulation. After catalyst addition, the formulation was maintained at 25° C. and the time in hours were recorded for the formulation to for a gel as an indication of "pot life". In addition coatings were made with each formulation and the time in hours at ambient temperature were recorded for the coating to achieve drying parameters of Sol-Gel transition and Surface Drying Time as measured with a B. K. Drying Recorder. The results are given in Table 1. Catalysts of the present invention preformed about as well as the industrial standard of DBTDL.

Example 2

Catalysis of blocked isocyanates for the production of polyurethane coatings was evaluated. Catalysts of the present invention (Formula 1, Expanded Formula 1 and Formula 2) were compared with a present industrial standard catalyst, dibutyltin dilaurate (DBTDL). Aliquots of a formulation of MEKO blocked HDI, an acrylic based polyol, in MAK (Methyl amyl ketone) and MIBK (methyl isobutyl ketone) solvents were prepared, each containing sufficient catalyst to constitute 0.14% catalyst based on the weight of tin and based on the total weight of solids in the formulation. The formulations were preheated to between 70 and 80 degrees C. so that the selected catalyst would be soluble in the formulation. After catalyst addition into the preheated formulation, the formulation was raised to 130 ° C. and the time in minutes were recorded for the formulation to reach the gel point (2,500 Centipoises) which indicates substantial completion of the reaction using a Brookfield Viscometer. The results are given in Table 2. Catalysts of the present invention preformed better then the industrial standard of DBTDL.

Example 3

Catalysis of blocked isocyanates for the production of polyurethane coatings was evaluated as in Example 2 in combination with a zinc containing co catalyst (zinc neodecanoate). Catalysts of the present invention (Formula 1, Expanded Formula 1 and Formula 2) with and without the cocatalyst were compared to a current industrial standard catalyst, DBTDL and to zinc neo decanoate. Aliquots of a formulation of an Acrylic based polyol, an Oxime blocked isocyanate, MAK and MIBK were prepared, each containing a quantity of catalyst indicated in Table 3 based on the weight of tin (zinc for zinc neodecanoate). The formulations were preheated if necessary so that the selected catalyst would be soluble in the formulation. After catalyst addition into the preheated formulation, the formulation was raised to 120° C. and the time recorded for the formulation to reach the gel point (2,500 Centipoises) which indicates substantial completion of the reaction. The results are given in Table 3. Catalysts of the present invention preformed better then the industrial standard of DBTDL and their performance was improved by the addition of the cocatalyst zinc neodecanoate.

Example 4

This example evaluates the effect of catalyst concentration on catalyst performance for catalysts of Expanded Formula 1 in comparison to DBTDL for the reaction of blocked isocyanates with a polyol for the production of polyurethane coatings. A catalyst of the present invention was compared with a present industrial standard catalyst, dibutyltin dilaurate (DBTDL). The catalyst used was a polystannoxane of the Expanded Formula 1 wherein each R is butyl and each $R^1$ is $OCOCF_3$, n is 0, and x is 0 which is consistent with a polystannoxane of the empirical formula $R_2SnAO$—$[R_2SnO]_x$—$SnR_2A$ $(H_2O)_n$ in which all the selections for R are butyl, A is the derivative of a strong organic acid and is $OCOCF_3$, x is 0 and n is about 0. Aliquots of a formulation of Desmophen A565, an acrylic polyol available from Bayer, Desmodur BI 3175A an oxime blocked isocyanate available from Bayer, MAK and MIBK were prepared, each containing sufficient various quantities of catalyst as stated in Table 4 (% catalyst based on the weight of tin and total weight of solids in the formulation). After catalyst addition into the preheated formulation, the formulation was raised to the temperature stated in Table 4 and the time in minutes recorded for the formulation to reach the gel point (2,500 Centipoises) which indicates substantial completion of the reaction. The results are given in Table 4. Catalysts of the present invention preformed better then the industrial standard of DBTDL even when the concentration of DBTDL was 250% higher Example 5

The ability of catalysts of the present invention to catalyze silicone polymerization was evaluated in comparison to DBTDL. The reactants were tetra propyl silicate as a cross linker for a silanol-terminated polydimethylsilicone oil. The formulation with the desired catalyst was heated to 140° C. In a stirred plastic beaker and the time in minutes to reach the gel point was recorded. Superior performance was obtained with the catalysts of the present invention except when the catalyst was not soluble in the reaction mixture. The results are given in Table 5.

Example 6

The ability of catalysts of the present invention to catalyze melamine formaldehyde crosslinking with acrylic polyol was evaluated in comparison to DBTDL and Nacure 5626 available from King Industries and is an amine blocked dodecylbenzene sulfonic acid. The formulation for each test used as reactants 60.2 grams of hexamethoxy melamine (Cymel 303) and 140.71 grams of an acrylic polyol (Joncryl 500) in 100 grams of methylethyl ketone (MEK). The formulation with the desired catalyst was heated to 140° C. in a stirred plastic beaker and the time in minutes to reach the gel point was recorded. Superior performance was obtained with the catalysts of the present invention in comparison to the comparative tin based catalyst, DBTDL. The results are given in Table 6.

Example 7

The ability of catalysts of the present invention to catalyze esterification and transesterification reactions was evaluated in comparison to dibutyltinoxide (DBTO) and butylstannoic acid (BSA). The reactants were phthalic anhydride and 2-ethylhexanol at a reaction temperature of 220° C. and with 5% excess alcohol. The formulation with the desired catalyst was maintained at 220° C. and the decrease in acid number was monitored with time (hours). Catalyst addition was on an equal weight of tin basis and at the rate of 100 milligrams of tin per 100 grams of phthalic anhydride. Completion is considered at an acid number below about 3. Superior performance was obtained with the catalysts of the present invention. The results are given in Table 7.

TABLE A

| Catalyst | Relative Rate |
| --- | --- |
| Dibutyltin dilaurate | 1.0 |
| $Bu_2Sn(OSO_2CH_3)_2$ [1] | Insoluble |
| $Bu_2Sn(pTSA)_2$ [2] | 0.17 |
| $[Bu_2Sn(pTSA)]_2O$ [3] | 0.07 |

[1] Formula 2, R and $R^2$ are butyl and $R^1$ are methylsulfonate
[2] Formula 2, R and $R^2$ are butyl and $R^1$ are p-toluene sulfonate
[3] Formula 1, R and $R^2$ are butyl, $R^1$ are p-toluene sulfonate, n = 0 and x is about 0

TABLE 1

Catalyst Performance in PolyUrethane Coating

| Catalyst | Sol-Gel Transition (hrs.) | Surface Dry Time (hrs.) | Pot Life (hrs.) |
| --- | --- | --- | --- |
| Dibutyltin dilaurate | 3.0 | 3.8 | 6.0 |
| $Bu_2Sn(OSO_2CH_3)_2$ [1] | 5.0 | 8.0 | 7.8 |
| $Bu_2Sn(pTSA)_2$ [2] | 3.0 | 6.5 | 6.0 |
| $[Bu_2Sn(pTSA)]_2O$ [3] | 3.0 | 4.0 | 5.0 |

[1] Formula 2, R and $R^2$ are butyl and $R^1$ are methylsulfonate
[2] Formula 2, R and $R^2$ are butyl and $R^1$ are p-toluene sulfonate
[3] Formula 1, R and $R^2$ are butyl, $R^1$ are p-toluene sulfonate, n = 0 and x is about 0

TABLE 2

| CATALYST | % TIN | GEL TIME @ 130 | GEL TIME @ 125 |
| --- | --- | --- | --- |
| DBTDL | 0.14 | 23.4 | |
| $Bu_2Sn(OCOCCl_3)_2$ [1] | 0.14 | 25.2 | |
| $\{Bu_2Sn(OCOCCl_3)\}_2O$ [2] | 0.14 | 14.9 | |
| $\{Bu_2Sn(OCOCF_3)\}_2O$ [3] | 0.14 | 15.1 | |
| $Bu_2Sn(OSO_2CH_3)_2$ [4] | 0.14 | 15.7 | |
| $\{Bu_2Sn(OSO_2CH_3)\}_2O$ [5] | 0.14 | 15.2 | |
| $\{Bu_2Sn(OSO_2CH_3)\}_2O$ [5] | 0.14 | | 22.6 |
| $\{Bu_2Sn(OSO_2CH_3)\}_2O$ [5] | 0.11 | | 26.2 |
| $\{Bu_2Sn(OSO_2CH_3)\}_2O$ [5] | 0.095 | | 30.4 |
| $\{Bu_2Sn(OSO_2CH_3)\}_2O$ [5] | 0.082 | | 33.4 |

[1] Formula 2, R and $R^2$ are butyl and $R^1$ are trichloroacetate
[2] Expanded Formula 1, R and $R^2$ are butyl, $R^1$ are trichloroacetate, n = 0 and x is about 0
[3] Expanded Formula 1, R and $R^2$ are butyl, $R^1$ are trifluoroacetate, n = 0 and x is about 0
[4] Formula 2, R and $R^2$ are butyl and $R^1$ are methylsulfonate
[5] Formula 1, R and $R^2$ are butyl, $R^1$ are methylsulfonate, n = 0 and x is about 0

TABLE 3

| CATALYST | % METAL | GEL TIME @ 120 C. | COMMENTS |
| --- | --- | --- | --- |
| Dibutyltin dilaurate | 0.2% Sn | 48.7 | |
| Zn neo decanoate | 0.35% Zn | >40 | |
| $Bu_2Sn(OSO_2CH_3)_2$ [1] | 0.2% Sn | 26.4 | sol at 70C |
| $Bu_2Sn(OSO_2CH_3)_2$ [1] + Zn neo decanoate | 0.2% Sn 0.07% Zn | 22.1 | sol at 70C |
| $\{Bu_2Sn(OCOCF_3)\}_2O$ [2] | 0.2% Sn | 27.3 | sol at 70C |
| $\{Bu_2Sn(OCOCF_3)\}_2O$ [2] Zn neo decanoate | 0.2% Sn 0.07% Zn | 20.4 | sol at 70C |
| $Bu_2Sn(OCOCCl_3)_2$ [3] | 0.2% Sn | 27.2 | sol at 40C |
| $Bu_2Sn(OCOCCl_3)_2$ [3] + Zn neo decanoate | 0.2% Sn | 13.4 | sol at 40C |
| $\{Bu_2Sn(OCOCCl_3)\}_2O$ [4] | 0.2% Sn | 25.5 | sol at 25C |
| $\{Bu_2Sn(OCOCCl_3)\}_2O$ [4] Zn neo decanoate | 0.2% Sn 0.07% Zn | 12.7 | sol at 25C |

[1] Formula 2, R and $R^2$ are butyl and $R^1$ are methylsulfonate
[2] Expanded Formula 1, R and $R^2$ are butyl, $R^1$ are trifluoroacetate, n = 0 and x is about 0
[3] Formula 2, R and $R^2$ are butyl and $R^1$ are trichloroacetate
[4] Expanded Formula 1, R and $R^2$ are butyl, $R^1$ are trichloroacetate, n = 0 and x is about 0

TABLE 4

Effect of Increase in Catalyst Concentration on Performance

| CATALYST | % Sn | Min @ 130° C. | Min @ 125° C. | Min @ 120° C. |
| --- | --- | --- | --- | --- |
| Dibutyltin dilaurate | 0.20 | 18.6 | | 48.7 |
| Dibutyltin dilaurate | 0.50 | 17.3 | | 33.5 |
| $\{Bu_2Sn(OCOCF_3)\}_2O$ [1] | 0.20 | 13.0 | 18.6 | 27.3 |
| $\{Bu_2Sn(OCOCF_3)\}_2O$ [1] | 0.5 | 11.8 | 16.2 | 24.0 |

1. Expanded Formula 1, R and $R^2$ are butyl, $R^1$ are trifluoroacetate, n = 0 and x is about 0

TABLE 5

| Cure T ° C. | Catalyst | g | Gel Time (min) |
| --- | --- | --- | --- |
| 140 | Dibutyltin dilaurate | 0.63 | 149.9 |
| 140 | $Bu_2Sn(OAc)_2$ [1] | 0.35 | 96.4 |
| 140 | $Bu_2OAcSnOSnOAcBu_2$ [2] | 0.44 | >130.0 (insoluble) |
| 140 | $Bu_2Sn(OCOCCl_3)_2$ [3] | 0.56 | 11.5 |
| 140 | $[Bu_2(OCOCCl_3)Sn]_2O$ [4] | 0.40 | 12.4 |
| 140 | $[Bu_2(OCOCF_3)Sn]_2O$ [5] | 0.35 | 10.7 |
| 140 | $Bu_2Sn(OCOCF_3)_2$ [6] | 0.46 | 8.8 |

[1] Formula 2, R and $R^2$ are butyl and $R^1$ are acetate
[2] Expanded Formula 1, R and $R^2$ are butyl, $R^1$ are acetate, n = 0 and x is about 0
[3] Formula 2, R and $R^2$ are butyl and $R^1$ are trichloroacetate
[4] Expanded Formula 1, R and $R^2$ are butyl, $R^1$ are trichloroacetate, n = 0 and x is about 0
[5] Expanded Formula 1, R and $R^2$ are butyl, $R^1$ are trifluoroacetate, n = 0 and x is about 0
[6] Formula 2, R and $R^2$ are butyl and $R^1$ are trifluoroacetate

TABLE 6

Melamine Crosslinking

| Catalyst | Solubility @ Room Temp. | Gel Time @ 115° C. (min) |
| --- | --- | --- |
| $Bu_2Sn(OSO_2CH_3)_2$ [1] | partly soluble | 6.1 |
| $\{Bu_2Sn(OSO_2CH_3)\}_2O$ [2] | partly soluble | 5.9 |
| Nacure 5625 (amine blocked sulfonic acid) | soluble | 6.4 |

TABLE 6-continued

Melamine Crosslinking

| Catalyst | Solubility @ Room Temp. | Gel Time @ 115° C. (min) |
| --- | --- | --- |
| Dibutyltin dilaurate | soluble | >100 |
| Dibutyltin oxide | soluble | >100 |

[1] Formula 2, R and $R^2$ are butyl and $R^1$ are methylsulfonate
[2] Formula 1, R and $R^2$ are butyl, $R^1$ are methylsulfonate, n = 0 and x is about 0
Catalysts added on equimolar basis
Catalysts conc = 0.18 mmol based on total wt of solids
Gel time measurements (Brookfield Viscometer) at 115° C.
Measure rate of viscosity increase to reach gel point (2500 cps)

TABLE 7

Acid Number vs. Time

| Time (hrs) | DBTO[1] | BSA[2] | BuSn(MSA)$_3$[3] | Bu$_2$Sn(MSA)$_2$[4] | (Bu$_2$SnMSA)$_2$O[5] | (Bu$_2$Sn pTSA)$_2$O[6] |
| --- | --- | --- | --- | --- | --- | --- |
| 0.5 | 63.9 | 60.5 | 27.5 | 32.2 | 41.8 | 43.6 |
| 1.0 | 40.5 | 69.1 | 10.5 | 15.8 | 23.2 | 22.6 |
| 1.5 | 29.2 | 23.0 | 5.3 | 9.1 | 14.2 | 14.2 |
| 2.0 | 22.4 | 12.1 | 3.3 | 5.6 | 9.2 | 9.3 |
| 2.5 | 17.5 | 7.6 |  | 3.8 | 6.5 | 5.9 |
| 3.0 | 13.4 | 4.7 |  |  | 3.9 | 3.8 |
| 3.5 | 10.1 |  |  |  |  |  |
| 4.0 | 7.2 |  |  |  |  |  |
| 4.5 | 5.3 |  |  |  |  |  |
| 5.0 | 3.8 |  |  |  |  |  |

[1]. Dibutyltin oxide
[2]. Butylstannoic acid
[3]. Formula 2, R is butyl and $R^1$ and $R^2$ are methylsulfonate
[4]. Formula 2, R and $R^2$ are butyl and $R^1$ are methylsulfonate
[5]. Formula 1, R and $R^2$ are butyl, $R^1$ are methylsulfonate, n = 0 and x is about 0
[6]. Formula 1, R and $R^2$ are butyl, $R^1$ are p-toluene sulfonate, n = 0 and x is about 0

We claim:

1. A polystannoxane salt of a strong organic acid having multiple catalytic activity, comprising a compound of the formula:

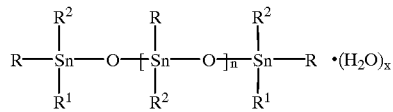

wherein each R is independently selected from the group consisting of alkyl having from 1 to 20 carbon atoms, aryl and alkaryl; each $R^1$ is independently selected from the group consisting of OR, OH, OOCR, halogen, and a derivative of a strong organic acid having a pKa of less than 1 provided that at least one selection for $R^1$ is OSO$_2$R, with each R having the same meaning as above; each $R^2$ being independently selected from the same groups as R and $R^1$; n is an integer having an average value from 0 to 20; and, x is from 0 to approaching infinity when the catalyst is in an aqueous solution.

2. The stannoxane of claim 1 wherein each $R^1$ is independently selected from the group consisting of OSO$_2$R, wherein R has the same meaning as R defined in claim 1; $R^3$COO wherein $R^3$ is an alkyl or aryl group in which the carbon atom bonded to the COO group contains at least one F, Cl, Br, I, CN attached to it; RPO$_3$H wherein R has the same meaning as R defined in claim 1; RCrO$_4$H wherein R has the same meaning as R defined in claim 1; F; NO$_3$; ClO$_4$; and, (NO)$_2$C$_6$H$_2$OH; provided that at least one selection for $R^1$ is OSO$_2$R.

3. An improved curable polymeric coating composition comprising or obtained by combining at least one set of polymer forming reactants selected from the group consisting of polyurethane forming reactants, silicone forming reactants, amino forming reactants and ester forming reactants; wherein the improvement comprises including in said composition an organotin salt of a strong organic acid as a catalyst for the reaction of said polymer forming reactants, said catalyst being selected from the group of organotin compounds corresponding to the formulas consisting of:

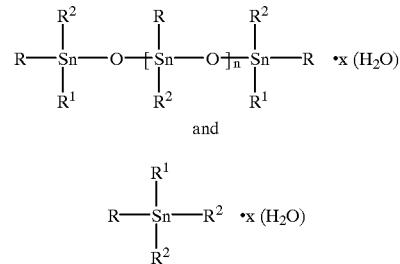

wherein each R is independently selected from the group consisting of alkyl having from 1 to 20 carbon atoms, aryl and alkaryl; each $R^1$ is independently selected from the group consisting of OR, OH, OOCR, halogen, and a derivative of a strong organic acid having a pKa of less than 1, with R having the same meaning as above; provided that at least one $R^1$ is derived from an organic acid having a pKa less than 1; each $R^2$ being independently selected from the same groups as R and $R^1$; n is an integer having an average value from 0 to 20; and, x is from 0 to approach infinity when the catalyst is in an aqueous solution.

4. The composition of claim 3 wherein each $R^1$ is independently selected from the group consisting of OSO$_2$R, wherein R has the same meaning as R defined in claim 1; $R^4$COO wherein $R^4$ is an alkyl or aryl group in which the carbon atom bonded to the COO group contains at least one F, Cl, Br, I, or CN attached to it; RPO$_3$H wherein R has the same meaning as R defined in claim 1; $RCrO_4H$ wherein R has the same meaning as R defined in claim 1; F; $NO_3$; $ClO_4$; and, $(NO)_2C_6H_2OH$; provided that at least one selection for $R^1$ is $OSO_2R$.

5. The composition of claim 3 wherein said set of polymer forming reactants is polyurethane forming reactants.

6. The composition of claim 3 wherein said set of polymer forming reactants is silicone polymer forming reactants.

7. The composition of claim 3 further comprising a zinc or tin containing cocatalyst.

8. The composition of claim 3 wherein said set of polymer forming reactants is amino resin forming reactants.

9. The composition of claim 3 wherein two sets of polymer forming reactants are combined in said composition.

10. The composition of claim 9 wherein said two sets of polymer forming reactants are amino polymer forming reactants and polyurethane forming reactants.

11. The composition of claim 10 wherein said amino forming reactants are melamine forming reactants.

12. An improved coating containing at least two layers comprising a first layer containing a coating composition of claim 3 and a second layer on top of and in contact with the first layer containing a coating composition of claim 3 but without the catalyst component of claim 3 or containing relatively less catalyst then the first layer.

13. An improved process for producing an organotin salt of a strong organic acid of the formula:

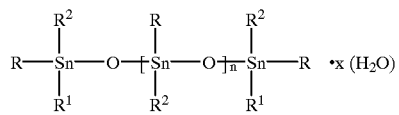

or

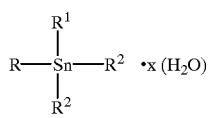

wherein each R is independently selected from the group consisting of alkyl having from 1 to 20 carbon atoms, aryl and alkaryl; each $R^1$ is independently selected from the group consisting of OR, OH, OOCR, halogen, and a derivative of a strong organic acid having a pKa of less than 1, with R having the same meaning as above; provided that at least one $R^1$ is derived from an organic acid having a pKa less than 1; each $R^2$ being independently selected from the same groups as R and $R^1$; n is an integer having an average value from 0 to 20; and, x is from 0 to approach infinity when the catalyst is in an aqueous solution; said process comprising reacting the reactants for said organotin salt in a solvent system; wherein the improvement comprises utilizing as the solvent system a mixture of at least two polar solvents with one solvent being water and the other solvent being an alcohol.

14. The improved process of claim 13 further comprising the steps of;

(a) cooling and crystallizing the stannoxane in said mixture of polar solvents;

(b) separating the stannoxane from said mixture; and, (c) drying the stannoxane to produce crystalline, granular, nontacky solid.

15. The crystalline, granular, nontacky solid produced by the process of claim 12.

16. An improved esterification or transesterification reaction product comprising a catalyst and reactants capable of entering into an esterification or transesterification reaction in the presence of the catalyst; wherein the improvement comprises including as the catalyst in said composition an organotin salt of a strong organic acid as a catalyst for the reaction of said polymer forming reactants, said catalyst being selected from the group of organotin compounds corresponding to the formulas consisting of:

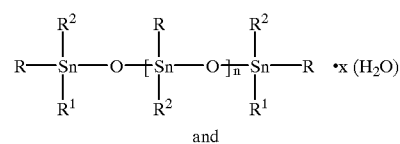

and

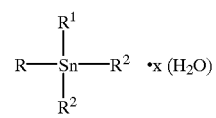

wherein each R is independently selected from the group consisting of alkyl having from 1 to 20 carbon atoms, aryl and alkaryl; each $R^1$ is independently selected from the group consisting of OR, OH, OOCR, halogen, and a derivative of a strong organic acid having a pKa of less than 1, with R having the same meaning as above; provided that at least one $R^1$ is derived from an organic acid having a pKa less than 1; each $R^2$ being independently selected from the same groups as R and $R^1$; n is an integer having an average value from 0 to 20; and, x is from 0 to approach infinity when the catalyst is in an aqueous solution.

17. The composition of claim 16 wherein each $R^1$ is independently selected from the group consisting of $OSO_2R$, wherein R has the same meaning as R defined in claim 1; $R^4$ COO wherein $R^4$ is an alkyl or aryl group in which the carbon atom bonded to the COO group contains at least one F, Cl, Br, I, or CN attached to it; $RPO_3H$ wherein R has the same meaning as R defined in claim 1; $RCrO_4H$ wherein R has the same meaning as R defined in claim 1; F; $NO_3$; $ClO_4$; and, $(NO)_2C_6H_2OH$; provided that at least one selection for $R^1$ is $OSO_2R$.

* * * * *